United States Patent [19]
Demarest et al.

[11] Patent Number: 5,487,308
[45] Date of Patent: Jan. 30, 1996

[54] NEEDLE AND SUTURE AUTOMATIC PULL-TEST SYSTEM

[76] Inventors: David Demarest, 709 S. Beverwyck Rd., Parsippany, N.J. 07054; Timothy Lenihan, 213 Valerie Rd., Morrisville, Pa. 19067; John F. Blanch, 141B Wayside Rd., Tinton Falls, N.J. 07724

[21] Appl. No.: 181,601

[22] Filed: Jan. 13, 1994

[51] Int. Cl.⁶ ................................................. G01N 3/10
[52] U.S. Cl. .................................................... 73/827
[58] Field of Search ........................... 73/826–828, 830, 73/831, 834, 837, 842, 845, 846, 856, 827; 29/517; 606/224, 225, 227

[56] References Cited

U.S. PATENT DOCUMENTS

| | | | |
|---|---|---|---|
| 2,736,194 | 2/1956 | Dilts | 73/827 |
| 2,782,635 | 2/1957 | Knight | 73/828 |
| 2,928,395 | 3/1960 | Forbes et al. | 606/227 |
| 3,611,551 | 10/1971 | Shave et al. | |
| 3,875,946 | 4/1975 | Duncan | 606/227 |
| 3,980,177 | 9/1976 | McGregor | |
| 4,072,041 | 2/1978 | Hoffman et al. | |
| 4,475,404 | 10/1984 | Rutledge, Jr. et al. | 73/827 |
| 4,722,384 | 2/1988 | Matsutani | |
| 4,806,737 | 2/1989 | Coates | |
| 4,832,025 | 5/1989 | Coates | |
| 4,922,904 | 5/1990 | Uetake et al. | |
| 4,924,709 | 5/1990 | Plyter | 73/830 |
| 5,226,336 | 7/1993 | Coates | |

Primary Examiner—Robert Raevis

[57] ABSTRACT

An automatic pull-testing apparatus for testing the strength of an armed surgical needle comprises a supporting blade for supporting a suture receiving end of the armed needle and having at least one suture receiving guide therein. A first gripping device is provided for releasably retaining the armed needle in an oriented position, and for positioning the armed needle at the supporting blade to enable the suture strand depending therefrom to be threaded at the suture receiving guide. A second suture gripping device grips the suture at a position below the suture receiving guide of the supporting blade. A slide block counterweighted to a predetermined weight is connected to the second suture gripping device for applying a controlled positive downward force upon the suture strand. When the first gripping device releases its grip upon the armed needle and the second gripping device and the slide block is released, a positive downward force is applied to the suture strand to perform a minimum pull-test of the armed needle. A destructive pull test is also performed by a device that generates a positive force against the slide block that is sufficient to dislodge the suture from the needle.

21 Claims, 4 Drawing Sheets

NEEDLE AND SUTURE AUTOMATIC PULL-TEST SYSTEM

FIELD OF THE INVENTION

The present invention relates generally to machines for automatically packaging surgical needle-suture combinations, i.e., armed-needles, and more specifically, to an apparatus and method for automatically testing the strength of an armed surgical needle to ensure that pull-test requirements are met prior to packaging thereof.

DESCRIPTION OF THE PRIOR ART

Currently, most armed surgical needles, i.e., needles having sutures attached to one end thereof, are manufactured utilizing manual and semi-automated procedures such as those described in U.S. Pat. Nos. 3,611,551, 3,980,177, and 4,922,904 which generally disclose devices that feed a length of suture material to the crimping end of a surgical needle (U.S. Pat. Nos. 3,980,177 and 4,922,904), and devices that swage the suture tip to the surgical needle.

U.S. Pat. No. 3,980,177 in particular discusses the requirement of the surgeon or medical personnel using the armed needle to be able to detach the needle from the suture after suturing to avoid the necessity of cutting the suture with scissors. The patent itself is drawn to a needle-suture combination that is characterized as having a straight pull-out value between 3 ounces and 26 ounces depending upon the size of the suture. This patent, however, does not disclose a means for testing the armed-needle to determine its pull-out value, i.e., the means for providing the force necessary to detach the needle from the suture.

U.S. Pat. No. 4,922,904 discloses a means for confirming whether a length of suture has been firmly connected to the surgical needle or not by applying tension to the suture after swaging thereof and prior to cutting the suture. No means or method is provided for determining the amount of force that is required to separate the needle from the suture.

However, it is desirable to provide an automatic pull-test system that is designed to determine whether a needle-suture combination meets the recommended minimum pull-test requirements as set forth by the medical profession.

Furthermore, it would be desirable to provide an automatic pull-test system that automatically determines whether the needle-suture combination meets the minimum pull-test requirements, and furthermore, one that is implemented in an automatic needle threading and swaging system that automatically cuts a predetermined length of suture material and automatically swages the suture to the needle.

It is also desirable to provide an automatic pull-test system that can perform minimum pull-testing and destructive pull-testing of the armed needle prior to packaging thereof.

Moreover, it would be desirable to provide an automatic pull-test system that is operated under the control of a control system computer that can perform minimum pull-testing of the armed needle without manual intervention and with a minimum amount of time expenditure.

SUMMARY OF THE INVENTION

Accordingly, it is an object of the instant invention to provide an automatic pull-test system that can automatically perform minimum pull-testing of the armed needle in a cost-effective manner and without manual intervention.

Furthermore, it is an object of the present invention to provide an automatic pull-test system, wherein the armed-needle is automatically indexed to an automatic pull-test station after the suture has been cut and swaged to the surgical needle, and prior to packaging thereof.

It is another object of the instant invention to provide a cost-effective automatic pull-test system that can perform a destructive pull-test of an armed surgical needle at a predetermined intervals, and moreover, that can retain the destructive pull-test values for statistical analysis thereof and statistical process control.

Still another object of the instant invention is to provide an automatic pull-test system that can perform a destructive pull-test of an armed needle and retain the maximum pull-test values thereof, and moreover, one that can provide automatic adjustment of the upstream swaging dies used to produce the armed needle in accordance with statistical process control values.

These and other objects of the present invention are attained with an automatic pull-test apparatus and system for automatically testing the strength of an armed needle having a suture attached thereto. The apparatus comprises a blade means for supporting a suture receiving end of the armed needle when a positive downward force is applied to the suture strand, and having at least one suture receiving guide therein. A first multi-axis gripping means is provided for releasably retaining the armed needle in an oriented position and for positioning the armed needle above the blade means to enable the suture strand depending therefrom to be threaded at the suture receiving guide therein. A second suture gripping means grips the suture strand at a position below the suture receiving guide of the blade means and is maintained at that position prior to applying the downward force. A slide block of predetermined weight is connected to the second suture gripping means for applying a positive downward force of a predetermined value upon the suture strand along the vertical axis defined by the suture strand. When the first gripping means releases its grip of the needle and the second gripping means engages the suture strand, a positive downward force is applied by the slide block for performing minimum or destructive pull-testing of the armed needle.

Further benefits and advantages of the invention will become apparent from a consideration of the following detailed description given with reference to the accompanying drawings, which specify and show preferred embodiments of the invention.

DETAILED DESCRIPTION OF THE PREFERRED EMBODIMENT

The process of arming surgical needles, i.e., drawing of the suture material, cutting predetermined lengths thereof, threading and swaging the cut suture material to the surgical needle, is described in further detail in copending patent application Ser. No. 08/181,595 (attorney docket No. 8924) and application Ser. No. 08/181,599 (attorney docket No. 8937) assigned to the same assignee of the present invention and incorporated by reference herein.

Figure 1:
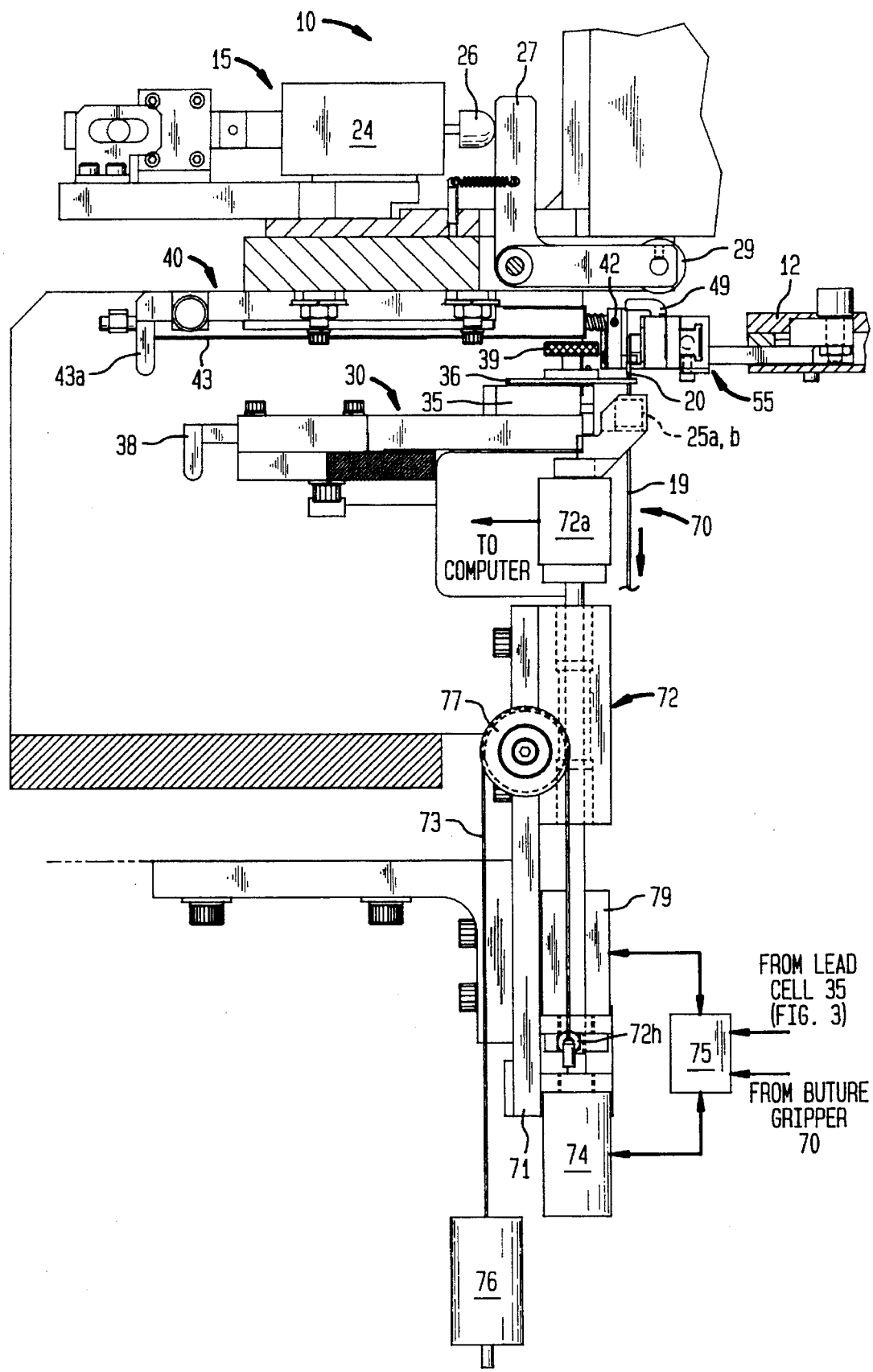
FIG. 1 is an assembly drawing of the automatic pull-test station 10 of the instant invention.
Figure 2A:
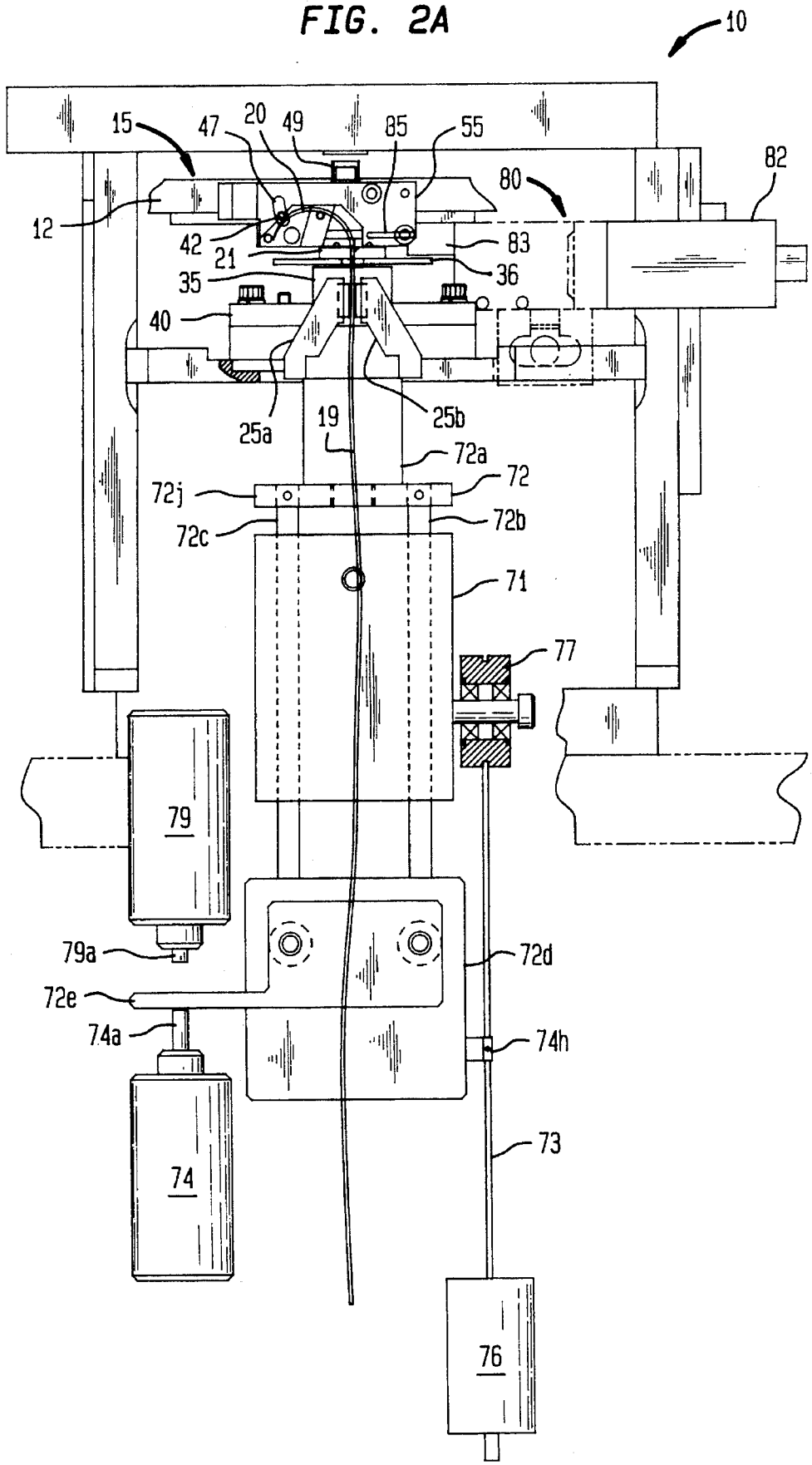
FIG. 2(a) is a front view of the automatic pull-test station 10 of the instant invention with the needle fence assembly 40 partially removed.
Figure 2B:
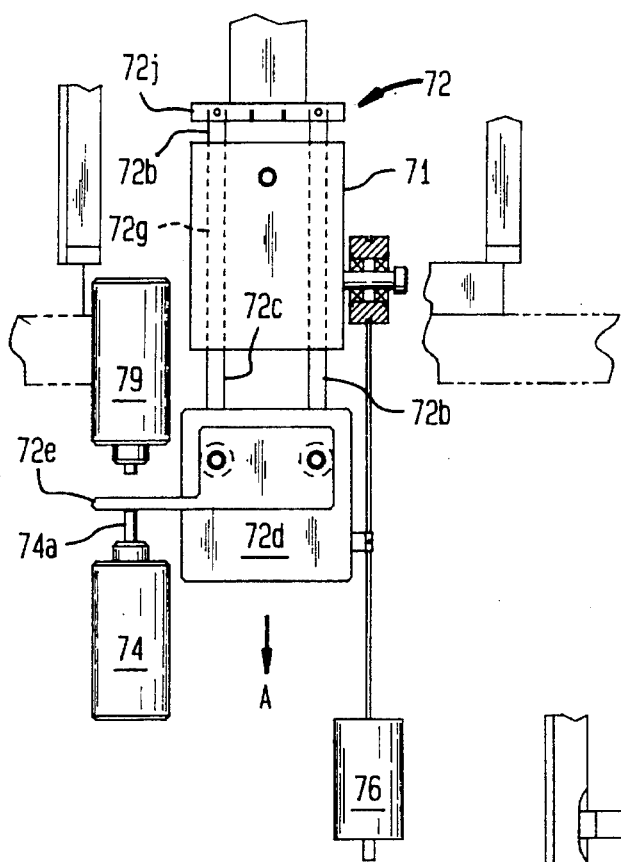
FIG. 2(b) is a detailed front view of the slide assembly means while performing a minimum pull-test.
Figure 2C:
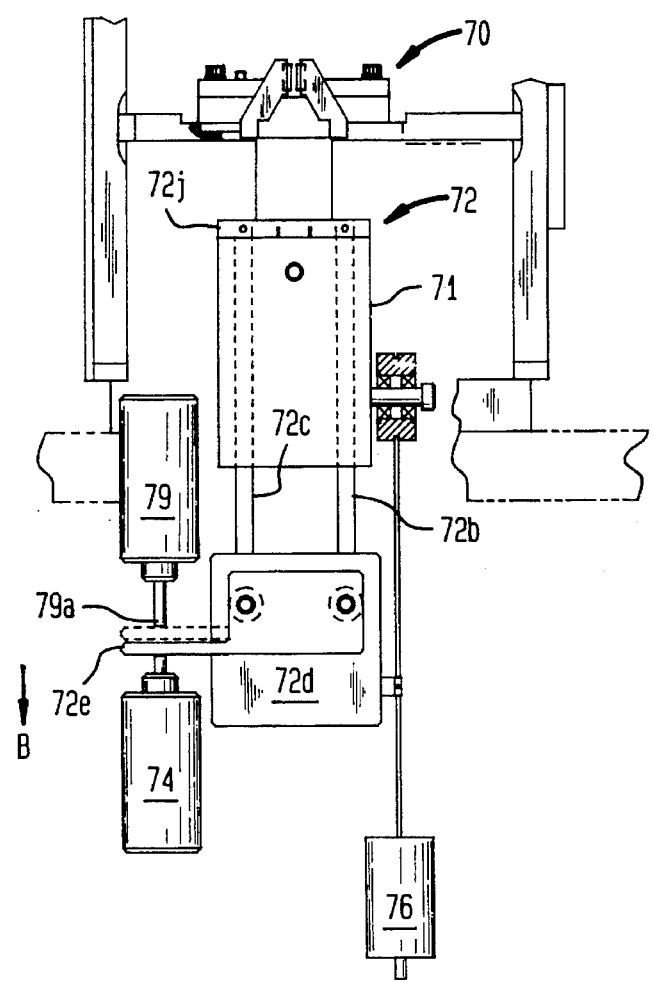
FIG. 2(c) is a detailed front view of the slide assembly means while performing a destructive pull-test.

The automatic pull-test assembly 10 for accomplishing automatic pull-testing of an armed surgical needle is shown generally in FIGS. 1 through 2(c). The automatic pull-test assembly 10 generally comprises a load cell mounting assembly 30 for mounting a load cell 35 which functions to receive the armed needle 20 from the multi-axis gripper 55 which is indexed thereto as shown in FIG. 1. A needle release assembly 15 is provided for relaxing the armed needle from the grip of the multi-axis gripper 55. Pull-test fence assembly 40 is provided to prevent the armed needle 20 from tipping over or becoming misaligned when the multi-axis gripper relaxes its hold on the armed needle. Suture gripping assembly 70 containing retractable gripper arms 25a,b for gripping the suture 19 during the pull-tests, and which are connected to the weighted slide block assembly 72 for performing the pull-test is provided as shown in FIG. 1. A detailed description of each of these assemblies and their interaction will be explained in detail hereinbelow.

As shown in FIGS. 1 and 2(a), an armed surgical needle 20 is retained by a multi-axis gripper 55 and is indexed to the automatic pull test assembly 10 by the rotary swage dial 12 partially illustrated in FIG. 2(a). The multi-axis gripper 55 is movable between an extended and retracted position relative to the pull-test station and details of the indexing operation of the rotary swage dial 12 and the retractable nature of the multi-axis gripper can be found in copending U.S. patent application Ser. No. 08/181,598 (attorney docket No. 8922) assigned to the present assignee of the instant invention and incorporated by reference herein.

Figure 3:
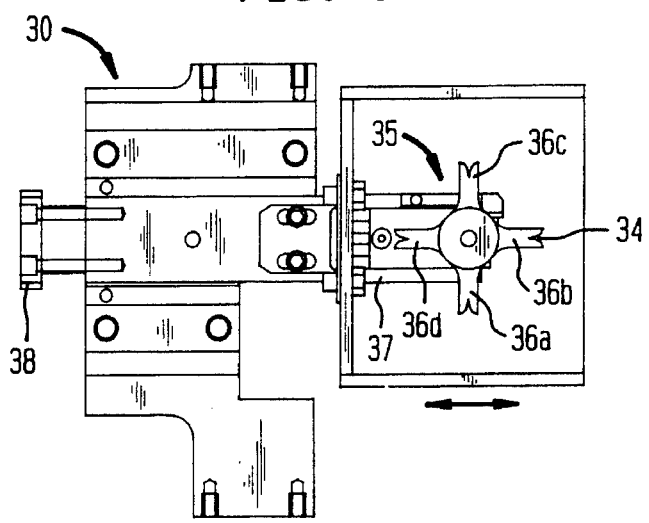
FIG. 3 is a top view of the load cell assembly 30 of the automatic pull-test assembly.

To position the armed needle 20 in the load cell 35, the multi-axis gripper is extended from the swage dial 12 so that the barrel portion 21 of needle 20 is positioned above a corresponding receiving blade of the load cell 35 as shown in FIG. 1. FIG. 3 illustrates a top view of the load cell mounting assembly 30 with load cell 35 mounted thereon. In the preferred embodiment, load cell 35 includes a flat disc (FIG. 1) comprising four thin needle supporting blades 36a,b,c,d for supporting the barrel portion 21 of various size surgical needles with the suture material 19 depending therefrom. For instance, load cell needle supporting blade 36a labelled "1/0" accommodates larger sutures having a diameter of approximately 0.017±0.001 inches; load cell needle receiving blade 36b labelled "2/0" accommodates sutures having a diameter of approximately 0.014±0.001 inches; load cell needle receiving blade 36c labelled "3/0" accommodates sutures having a diameter of approximately 0.011±0.001 inches; and load cell needle receiving blade 36d labelled "4/0" accommodates a smaller suture with a diameter of approximately 0.009±0.001 inches in the preferred embodiment. Depending upon the batch of surgical needles currently being pull tested, the appropriate receiving blade 36a,b,c,d will be positioned to receive the needle from the multi-axis gripper. Knob 39 located centrally on top of the load cell 35 may be manually operated to rotate the load cell blades and position the correct sized needle receiving blade prior to carrying out automatic pull-testing. Additionally, the load cell 35 may be laterally positioned by moving slide handle 38 and consequently load cell carriage 37 towards or away from the suture needle indicated by the arrow in FIG. 3.

Figure 4:
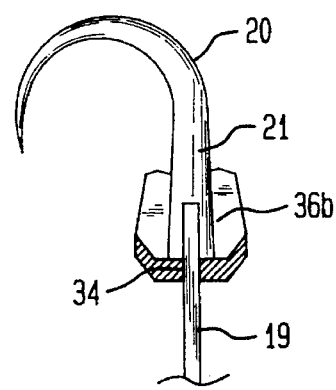
FIG. 4 is an enlarged view of an armed needle 20 supported by the suture receiving blade 36b of the load cell 35 with the suture threaded between the suture receiving opening 34.

The multi-axis gripper 55 is initially positioned so that the barrel portion 21 of armed needle 20 is supported by the appropriate needle supporting blade 36 (e.g. blade 36b). FIG. 4 is a front cross sectional view illustrating the barrel portion 21 of needle 20 resting upon the needle supporting blade 36b with the suture strand 19 threaded between the suture receiving opening 34.

Non-destructive pull testing of the armed surgical needle 20 is accomplished as follows:

After positioning the multi-axis gripper as heretofore described, gripper arms 25a,b of suture gripping assembly 70 are extended from a retracted position to grip the suture strand 19 slightly below the needle supporting blade 36 of load cell 35 as shown in FIG. 1. A gripper actuator 72a is provided for opening and closing gripper arms 25a,b, as shown in FIG. 1, and is controlled by a control system program resident in control system computer 75 as explained in further detail in copending patent application Ser. No. 08/181,607 (attorney docket No. 8927) assigned to the same assignee of the present invention. FIGS. 1 and 2(a) illustrate the slide assembly including slide block mount 72 that is composed of slide rods 72b,c that are connected to a lower slide block 72d. Slide block 72d includes a slide finger 72e upon which air cylinder piston rods 74a and 79a, of respective air cylinders 74, 79, apply respective upward and downward forces depending upon the type of pull-test that is to be performed. As shown in FIG. 2(a), piston rod 74a is shown in an extended position providing an upward force that supports slide finger 72e and consequently maintains slide block 72d of slide assembly 72 at a fixed vertical position.

Slide block 72d is counterweighted to a net downward weight of 2 to 5 ounces by appropriately sized counterweight 76 that acts through cable 73, around pulley 77, and through attachment point 72h. This counterweight 76 acts to pull upward on slide block 72d at the attachment point 72h.

To accomplish the non-destructive pull test, piston rod 74a of air cylinder 74, mounted on the mechanism frame 71 and controlled by system computer 75, is retracted from its extended position (FIG. 2(a)) supporting the slide finger 72e as shown in dashed line in FIG. 2(b), by reversing its air supply (not shown), to the position shown in the figure. The piston rod 74a is retracted to remove the upward force on slide finger 72e, as shown in the FIG. 2(b), to thereby impose the counterbalanced net weight of 2 to 5 ounces of slide block 72d on the swage attachment means of suture 19 in needle 20, in the direction of arrow "A". Accuracy of this system is enhanced because slide block 72d, suspended on slide rods 72b,c, are mounted in low friction ball bushings, 72f and 72g, that are pressed into slide mount 71, thereby imposing minimal mechanical drag on the system.

Note in FIG. 1, that the slide block mount 72 is positioned parallel to the axis of the suture 19 depending from the needle 20, and is located a distance away from the suture 19 corresponding to the length of the gripper arms 25a,b.

Simultaneous with or momentarily before the slide assembly 72 is released, the needle release assembly 15 is actuated to enable multi-axis gripper 55 to disengage its grip on the armed needle 20. Releasing the armed needle from the grip of the gripper 55 is necessary to ensure that it is firmly positioned on the load cell needle supporting blade 36. Moreover, to provide an accurate pull-test, the needle must be released so that there is no existing upward force that would cause false results.

As shown in FIG. 1, needle release assembly 15 comprises needle release solenoid 24 that is actuated to extend pusher 26 into pivotal lever arm 27. Pivotal lever arm 27 pivots about pin 28 to depress plunger 49 of the multi-axis gripper 55 at one end 29 thereof. As shown in FIG. 2, depressing plunger 49 enables pin 42 to retract within pin guide 47 to release the armed needle 20 engaged thereby. Further details of the operation of the multi-axis gripper 55 can be found in the above-mentioned copending patent application Ser. No. 08/181,599 (attorney docket 8937).

To prevent the armed needle 20 from becoming misaligned or from tipping over after the multi-axis gripper 55 releases its grip on the needle, a needle fence assembly 40 is provided. As shown in FIG. 2(a), the needle fence assembly 40 includes vertical fence plate 43 which can be adjusted to lie flush against the gripper 55 to retain the armed needle in an upright position. Adjusting the lateral positioning of the vertical fence plate 43 is accomplished by moving slide handle 43a for an appropriate distance as shown in FIG. 1. In the preferred embodiment, the configuration of the face of the vertical needle fence plate 42 (not shown) may be changed to accommodate the configurations of different size needles:

The controlled release of the minimum pull-test is of short duration, preferably ranging in milliseconds. If the test is successful, i.e., the suture meets the minimum pull-test requirements, the needle is re-gripped by the multi-axis gripper 55 by deactuating the needle release solenoid 24 (FIG. 1) which releases the force on plunger 49. The suture grippers 25a,b are then retracted to their open position to release their grip on the suture 19 as controlled by the control system. Subsequently, the multi-axis gripper 55 is retracted and the rotary swage dial is rotated to convey the armed needle downstream for further processing.

Figure 5:
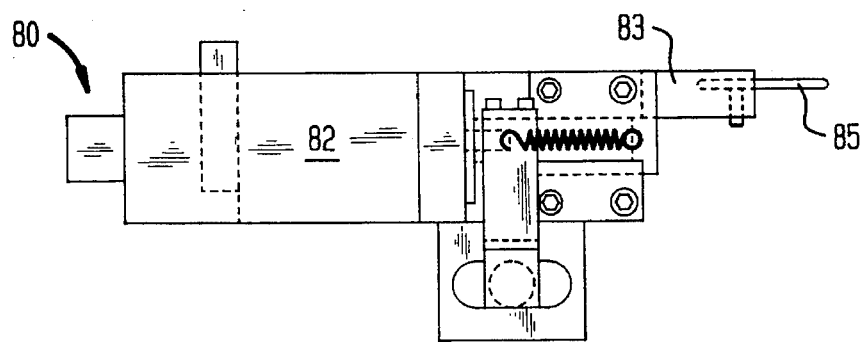
FIG. 5 is a detailed view of the needle stripper assembly 80 for removing the needle 20 after a destructive pull-test or after minimum pull-test failure.

If the suture fails the minimum pull-test, i.e., if the suture 19 is dislodged from the surgical needle 20 as a result of the controlled release, the control system computer 75 is flagged so that the disarmed needle 20 will be ejected at the pull-test station. The dislodged suture strand 19 will be drawn into a vacuum assembly (not shown) and the needle 20 will be ejected by a needle stripper assembly 80 shown generally in FIG. 2(a) and in detail in FIG. 5. As shown in FIG. 5, needle stripper solenoid 82 will be actuated by a control signal output from the control system computer 75 to extend needle stripper blade 85 mounted on a slide block 83. The needle stripper blade 85 is shown in FIG. 1 located next to the needle 20. Thus, when the needle is in its relaxed state on the multi-axis gripper 55 and the minimum pull-test fails, the needle stripper blade 85 is extended to remove the needle from the gripper. The needle will fall and be collected by appropriate collection means (not shown) located at the pull-test station.

To prepare for the next armed needle to be pull-tested, the slide assembly 72 and retracted gripper arms 25a,b are pushed back up the slide mount 71 to their unloaded position by an appropriate upward force supplied by the air cylinder 74 and piston rod 74a as controlled by the control system computer 75. At this time, another flag may be sent for storage to the control system computer that indicates that the pull-test performed on the particular needle 20 was successful and that the armed needle may be conveyed downstream for packaging thereof.

In the preferred embodiment of the minimum and destructive pull-test systems shown in FIGS. 1–3, the load cell 35 and the needle support blades 36a,b,c,d thereof comprise a piezoelectric transducer that measures the force applied by the suture gripping assembly to the needle-suture assembly 19. The transducer load cell 35 may be interfaced with the control system computer 75 by conventional means as shown in FIGS. 1 and 3, and, in the preferred embodiment, is a 1000 gram transducer manufactured by Techniques Co. (Model No. GS-1K). The forces applied to the suture 19 and measured by the load cell transducer 35 during the destructive pull-testing may be stored for statistical purposes or for real-time monitoring during a swage die setup routine that may take place when a new batch of surgical needles are to be swaged. For instance, if the destructive pull-tests fail and the forces measured by the transducer are determined to be at the low end of a predetermined range, then the control system computer 75 will acknowledge this and send appropriate signals to the upstream swaging assembly (not shown) causing a fixed swaging die to be advanced an incremental amount toward the moveable swage die, resulting in subsequent swages being stronger. Likewise, if the destructive pull-test passes, i.e., the forces measured by the transducer are determined to be above the minimum and below an upper limit, then no die adjustment need be made.

As previously mentioned, the automatic pull-test assembly 10 is used to perform a minimum pull-test upon every armed surgical needle indexed thereto prior to automatic packaging thereof. A destructive pull-testing of the armed surgical needle is performed at every nth needle indexed thereto. The purpose of performing a destructive pull-test is to set the swage dies located at the upstream swaging station for correct maximum swage pull-out value. This is by necessity a destructive test, and the test frequency, which is programmable, is set high enough to maintain control of the operation, but low enough to avoid excessive product waste. In the preferred embodiment, this frequency is set at every 50th needle, but could be every 75th or 100th needle.

Another purpose of the destructive pull test is to aid in installing a new swage die set during a changeover procedure, which is a procedure that is used to prepare the needle sorting and swaging apparatuses (swage dies) for processing a new batch of needles when they are of a different size from a previously processed batch. Contrary to the non-destructive pull-test described above, the pull-test apparatus is programmed for 100% destructive test of a swaged needle, while the swaging assembly is operating and feeding the armed needles to the pull-test station. The die adjustment system at the upstream swaging assembly will receive a signal from the transducer load cell 35, at each machine cycle, and quickly perform a correct adjustment of the swage dies.

Destructive test pull-out values are recorded in the system computer 75 and are used to compute statistical process control information which is fed back to the machine operator through display screens.

Destructive pull testing of the armed surgical needle 20 is accomplished similarly as described herein above with respect to the minimum pull test. However, the fundamental difference is that a fixed mechanical stroke that is great enough to pull the suture out of the needle replaces the minimum 2 to 5 ounce force of the minimum pull test.

As shown in FIG. 2(c), piston rod 79a of second air cylinder 79 located opposite air cylinder 74, is programmed to provide a fixed stroke against slide finger 72e from a non-actuating position shown in FIG. 2(a) to the position shown in FIG. 2(c). This results in the vertical displacement of slide finger 72e from a position shown by the dashed line to a position shown by the solid line. This further results in a downward force upon slide block 72d, which, through slide rods 72b and 72c, moves slide assembly 72, including grippers 25a,b and suture 19, in the direction of the arrow "B" as shown in FIG. 2(c). Air pressure to cylinder 79 is set high enough to always pull suture 19 out of needle 20. This stroke is limited by the underside of top portion 72j of slide assembly 72 striking the top of stationary block 71.

The force necessary to accomplish the destructive pull-test is measured by the piezoelectric load cell transducer 35 as discussed above. If it is determined by the process control algorithm (not shown) that the destructive pull-test forces as measured by the transducer load cell are lower than a predetermined range of pull-test values, the control system computer 75 will send out appropriate control signals to increase the swaging die stroke applied when swaging the suture to the needle at the upstream swaging station. If it is determined that the destructive pull-test forces as measured by the transducer load cell are higher than the predetermined range, the control system computer 75 will send out appropriate control signals to the upstream swaging assembly to move a fixed swage die a small incremental distance away from the suture, thereby decreasing the swaging pressures applied when swaging the suture to the needle.

Since the destructive pull-test necessarily results in the suture 19 becoming dislodged from the needle 20, the needle 20 is again removed from the grip of the multi-axis gripper 55 by the needle stripper blade 85 as described above. Subsequently, the gripper arms 25a,b are retracted to their open positions and air cylinder 74 provides the upward force to restore the gripping assembly 70 and slide block assembly 72 back to their normal position in preparation for the next pull-test.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed:

1. An apparatus for automatically testing the swage bond strength of an armed needle having a suture strand depending from a suture receiving end thereof, said apparatus comprising:
   (a) blade means for supporting said suture receiving end of said armed needle when a positive downward gravitational force of predetermined controllable value is applied to said suture strand, said blade means having at least one suture receiving guide therein;
   (b) indexing means for releasably engaging said armed needle and for positioning said armed needle at said blade means to enable said suture strand to be received within said suture receiving guide thereof; and
   (c) gripping means for positively gripping said suture strand at a first position below said suture receiving opening of said blade means, said gripping means including a vertically suspended slide block means consisting of a mass of predetermined weight for applying said positive downward force of predetermined value to said gripped suture strand, said gripping means and said slide block means being vertically slidably mounted along a fixed mounting means, said fixed mounting means being positioned substantially parallel with a vertical axis defined by said suture strand.

2. The apparatus for automatically testing the swage bond strength of an armed needle according to claim 1 further including a means for maintaining said gripping means and said slide block means at a first position along said mounting means prior to applying said positive downward force to said gripped suture.

3. The apparatus for automatically testing the swage bond strength of an armed needle according to claim 2 wherein said maintaining means includes a first air cylinder means for applying pressure against a first side of said slide block means to maintain said gripping means and said slide block means thereof at said first position.

4. The apparatus for automatically testing the swage bond strength of an armed needle according to claim 3 wherein said pressure applied to said first side of said slide block means is ceased to enable said slide block means to slide along said mounting means to a second position that is lower than said first position to effect said positive downward force to said gripped suture.

5. The apparatus for automatically testing the swage bond of said armed needle according to claim 4 further including a means for applying a positive downward force against a second side of said slide block means that is sufficient to dislodge said suture from said needle.

6. The apparatus for automatically testing the swage bond strength of an armed needle according to claim 5, further including means for measuring the value of said positive downward force applied by said slide block means to said gripped suture strand.

7. The apparatus for automatically testing the swage bond strength of an armed needle according to claim 6, wherein said measuring means includes a transducer means for measuring the deflection of said blade means when said positive downward force is applied to said gripped suture strand.

8. The apparatus for automatically testing the swage bond strength of an armed needle according to claim 7 further including a computer control means connected with said transducer means for outputting a test fail signal if said suture becomes dislodged from said needle after application of said downward force.

9. The apparatus for automatically testing the swage bond strength of an armed needle according to claim 8 wherein said computer control means utilizes said measured value of said positive downward force for process control.

10. The apparatus for automatically testing the swage bond strength of an armed needle according to claim 1, wherein said slide block means further includes a means for controlling the application of said downward force applied to said suture strand.

11. The apparatus for automatically testing the swage bond strength of an armed needle according to claim 10, wherein said means for controlling the application of said downward force is a counterweight means, positioned to oppose a gravitational force generated by said slide block means.

12. The apparatus for automatically testing the swage bond strength of an armed needle according to claim 1 further including a plurality of said blade means selectively positionable by said indexing means in said apparatus for each supporting armed surgical needles having different barrel sizes.

13. The apparatus for automatically testing the swage bond strength of an armed needle according to claim 1, wherein said gripping means includes a pair of retractable gripper arms.

14. The apparatus for automatically testing the swage bond strength of an armed needle according to claim 1, further including means for measuring the value of said positive downward force applied by said slide block means to said gripped suture strand.

15. The apparatus for automatically testing the swage bond strength of an armed needle according to claim 14, wherein said measuring means includes a transducer means for measuring the deflection of said blade means when said positive downward force is applied to said gripped suture strand.

16. The apparatus for automatically testing the swage bond strength of an armed needle according to claim 14 further including a computer control means connected with said transducer means for outputting a test fail signal if said suture becomes dislodged from said needle after application of said downward force.

17. The apparatus for automatically testing the swage bond of said armed needle according to claim 15, said apparatus further including means for removing said needle from said gripping means upon receipt of said test fail signal from said computer control means.

18. The apparatus for automatically testing the swage bond of said armed needle according to claim 1, wherein said indexing means is actuated to release its engagement of said needle as said gripping means applies said positive downward force of predetermined value to said suture strand to thereby test the strength of said swage bond.

19. A method for automatically testing the attachment strength of an armed surgical needle having a suture strand depending therefrom, said method comprising the steps of:

(a) positioning a suture receiving end of said armed needle above a blade means for supporting said needle, wherein a first gripper means is gripping said armed needle in an oriented position above said blade means;

(b) positively gripping said depending suture strand at a first position below said blade means with a second gripper means, said second gripper means having a predetermined weight means connected thereto; and (c) generating a positive downward gravitational force upon said suture strand gripped by said second gripper means while concurrently releasing said armed needle from the grip of said first gripper means to enable said weight means to impart a downward tensile force to said needle and suture.

20. The method for automatically testing the attachment strength of an armed surgical needle according to claim 19 further including the step of measuring the value of said force applied to said suture strand.

21. The method for automatically testing the attachment strength of an armed surgical needle according to claim 20 further including the step of comparing said measured force value with predetermined values and generating a test fail signal if the measured value is not within a predetermined range.

* * * * *

UNITED STATES PATENT AND TRADEMARK OFFICE
CERTIFICATE OF CORRECTION

PATENT NO. : 5,487,308
DATED : January 30, 1996
INVENTOR(S) : David Demarest, et al.

It is certified that error appears in the above-indentified patent and that said Letters Patent is hereby corrected as shown below:

On the Title Page, after item [76], insert the following; -- [73] Assignee: Ethicon, Inc. --

Signed and Sealed this

Thirteenth Day of August, 1996

Attest:

BRUCE LEHMAN

Attesting Officer

Commissioner of Patents and Trademarks